US010479764B2

(12) United States Patent
DeLuca et al.

(10) Patent No.: US 10,479,764 B2
(45) Date of Patent: Nov. 19, 2019

(54) 2-METHYLENE-(22E)-25-HEXANOYL-24-OXO-26,27-CYCLO-22-DEHYDRO-19-NOR-VITAMIN D ANALOGS

(75) Inventors: Hector F. DeLuca, Deerfield, WI (US); Margaret Clagett-Dame, Deerfield, WI (US); Lori A. Plum, Arena, WI (US); Rafal Barycki, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 13/533,018

(22) Filed: Jun. 26, 2012

(65) Prior Publication Data

US 2013/0005686 A1 Jan. 3, 2013

Related U.S. Application Data

(60) Provisional application No. 61/502,123, filed on Jun. 28, 2011.

(51) Int. Cl.
*C07C 401/00* (2006.01)
*A61K 31/593* (2006.01)

(52) U.S. Cl.
CPC .......... *C07C 401/00* (2013.01); *A61K 31/593* (2013.01); *C07C 2601/02* (2017.05); *C07C 2601/14* (2017.05); *C07C 2602/24* (2017.05)

(58) Field of Classification Search
CPC .......................... C07C 401/00; C07C 2602/24
USPC ....................................................... 552/653
See application file for complete search history.

(56) References Cited

U.S. PATENT DOCUMENTS

| | | | |
|---|---|---|---|
| 4,666,634 A | 5/1987 | Miyamoto et al. |
| 5,063,221 A | 11/1991 | Nishii et al. |
| 5,086,191 A | 2/1992 | DeLuca et al. |
| 5,536,713 A | 7/1996 | DeLuca et al. |
| 5,545,633 A | 8/1996 | Bretting |
| 5,843,928 A | 12/1998 | DeLuca et al. |
| 5,929,056 A | 7/1999 | Mourino et al. |
| 5,945,410 A | 8/1999 | DeLuca et al. |
| 6,399,797 B1 | 6/2002 | von Daehne et al. |
| 6,566,352 B1 | 5/2003 | DeLuca et al. |
| 6,579,861 B2 | 6/2003 | DeLuca et al. |
| 6,627,622 B2 | 9/2003 | DeLuca et al. |
| 7,713,953 B2 | 5/2010 | DeLuca et al. |
| 9,834,512 B2 | 12/2017 | DeLuca |

FOREIGN PATENT DOCUMENTS

WO 9700242 1/1997

OTHER PUBLICATIONS

Ostrem et al, 24- and 26-homo-1,25-dihydroxyvitamin D3: Preferential Activity in Inducing Differentiation of Human Leukemia Cells HL-60 in vitro, Proc. Natl. Acad. Sci. USA, vol. 84, pp. 2610-2614, May 1987.

Perlman et al, 1alpha,25-dihydroxyvitamin D3, A Novel Vitamin D-related Compound with Potential Therapeutic Activity, Tetrahedron Letters, vol. 31, No. 13, pp. 1823-1824, 1990.
Okano et al, Regulatory Activites of 2beta-(3-Hydroxypropoxy)-1alpha,25-Dihydroxyvitamin D3, A Novel Synthetic Vitamin D3 Derivative, on Calcium Metabolism, Biochem. Biophys. Res. Commun., vol. 163, No. 3, pp. 1444-1449, Sep. 29, 1989.
Miyamoto et al, Synthetic Studies of Vitamin D Analogs. XIV. Synthesis and Calcium Regulating Activity of Vitamin D3 Analogs Bearing a Hydroxyalkoxy Group at the 2beta-Position, Chem. Pharm. Bull., vol. 41, No. 6, pp. 1111-1113, Jun. 1993.
Nishii et al, The Development of Vitamin D3 Analogs for the Treatment of Osteoporosis, Osteoporosis International (1993) Suppl., vol. 1, pp. 190-193.
Posner et al, Stereocontrolled Total Synthesis of Calcitrol Derivatives: 1,25-Dihyroxy-2-(4'-hydroxybutyl)vitamin D3 Analogs of an Osteoporosis Drug, J. Org. Chem., vol. 59, pp. 7855-7861, 1994.
Posner et al, 2-Fluoroalkyl A-Ring Analogs of 1,25-Dihyroxyvitamin D3. Stereocontrolled Total Synthesis via Intramolecular and Intermolecular Diels-Alder Cycloadditions. Preliminary Biological Testing, J. Org. Chem., vol. 60, pp. 4617-4626, 1995.
Lythgoe et al, Calciferol and its Relatives. Part 22. A Direct Total Synthesis of Vitamin D2 and Vitamin D3. J. Chem. Soc. Perkin I., pp. 590, 1978.
Lythgoe, Synthetic Approaches to Vitamin D and its Relatives. Chem. Soc. Rev., vol. 9, pp. 449, 1983.
Toh et al, Studies on a Convergent Route to Side-Chain Analogues of Vitamin D:25-Hydroxy-23-oxavitamin D3. J. Org. Chem., vol. 48, pp. 1414-1417, 1983.
Baggiolini et al, Stereocontrolled Total Synthesis of 1 [alpha],25-Dihydroxycholecaliferol and 1 [alpha],25-Dihydroxyergocalciferol. J. Org. Chem., vol. 51, pp. 3098-3108, 1986.
Sardina et al, Studies on the Synthesis of Side-Chain Hydroxylated Metabolites of Vitamin D. 2. Stereocontrolled Synthesis of 25-Hydroxyvitamin D2. J. Org. Chem., vol. 51, pp. 1264-1269, 1986.
Arbour et al, A Highly Sensitive Method for Large-Scale Measurements of 1,25-Dihydroxyvitamin D. Analytical Biochem., vol. 255, pp. 148-154, 1998.

(Continued)

*Primary Examiner* — Barbara P Badio
(74) *Attorney, Agent, or Firm* — Quarles & Brady LLP

(57) ABSTRACT

This invention discloses 2-methylene-(22E)-25-hexanoyl-24-oxo-26,27-cyclo-22-dehydro-19-nor-vitamin D analogs, and specifically 2-methylene-(22E)-25-hexanoyl-24-oxo-26,27-cyclo-22-dehydro-19-nor-1α-hydroxyvitamin $D_3$, and pharmaceutical uses therefor. This compound exhibits relatively high transcription activity as well as pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also shows low activity in vivo on bone calcium mobilization, and therefore may be used to treat autoimmune disorders or inflammatory diseases in humans as well as renal osteodystrophy. This compound may also be used for the treatment or prevention of obesity.

53 Claims, 7 Drawing Sheets

(56) References Cited

OTHER PUBLICATIONS

Collins et al, Normal Functional Characteristics of Cultured Human Promyelocytioc Leukemia Cells (HL-60) After Induction of Differentiation by Dimethylsulfoxide. The Journal of Experimental Medicine., vol. 149, pp. 969-974, 1979.

Darwish et al. Identification of a Transcription Factor That Binds to the Promoter Region of the Human Parathyroid Hormone Gene. Archives of Biochem and Biophysics., vol. 365, pp. 123-130, 1999.

Perlman et al, Novel Synthesis of 19-Nor-Vitamin D Compounds, Tetrahedron Letters, vol. 32, No. 52, pp. 7663-7666, 1991.

International Search Report and Written Opinion, PCT International Application No. PCT/US2012/044130, dated Sep. 5, 2012.

International Preliminary Report on Patentability, PCT International Application No. PCT/US2012/044130, dated Jan. 16, 2014.

Mayer et al., "Isolation and identification of 1,25-dihydroxy-24-oxo-vitamin D3 and 1,23,25-trihydroxy-24-oxo-vitamin D3. New metabolites of vitamin D3 produced by a C-24 oxidation pathway of metabolism for 1,25-dihydroxyvitamin D3 present in intestine and kidney", J. Biol. Chem., 1983, 258:13458-13465.

2-METHYLENE-(22E)-25-HEXANOYL-24-OXO-26,27-CYCLO-22-DEHYDRO-19-NOR-VITAMIN D ANALOGS

BACKGROUND OF THE INVENTION

This invention relates to vitamin D compounds, and more particularly to 2-methylene-(22E)-25-hexanoyl-24-oxo-26,27-cyclo-22-dehydro-19-nor-vitamin D analogs and their pharmaceutical uses.

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of several 19-nor-analogs (e.g., 1α,25-dihydroxy-19-nor-vitamin $D_3$) revealed a selective activity profile with high potency in inducing cellular differentiation, and reduced calcium mobilizing activity. Thus, some of these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1.993); Nishii et al., Osteoporosis Int. Suppl. 1, 190 (1993); Posner et. al., J. Org. Chem. 59, 7855 (1994), and J. Org. Chem. 60, 4617 (1995)), as have analogs with a cyclopropyl group in the side chain (e.g. MC-903 known as calcipotriene and described in Nishii et al U.S. Pat. No. 5,063,221).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at both carbon 1 (C-1) and carbon 3 (C-3), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

17-ene vitamin D compounds as well as vitamin D compounds having a double bond in the side chain thereof are also known, and have been proposed for various pharmacological uses. Bone diseases such as osteoporosis, skin disorders such as psoriasis, cancers such as leukemia and cosmetic conditions such as wrinkles are just some of the applications proposed for such compounds. 17-ene compounds are described in U.S. Pat. Nos. 5,545,633; 5,929,056 and 6,399,797 while 2-alkylidene compounds having a side chain with a double bond therein are described in, for example, U.S. Pat. No. 5,843,928.

SUMMARY OF THE INVENTION

The present invention is directed toward 2-methylene-(22E)-25-hexanoyl-24-oxo-26,27-cyclo-22-dehydro-19-nor-vitamin D analogs, their biological activity, and various pharmaceutical uses for these compounds. These new vitamin D compounds not known heretofore are the 19-nor-vitamin D analogs having a methylene group at the 2-position (C-2), an oxo group attached to carbon 24 (C-24) of the side chain, a double bond located between carbon atoms 22 and 23 in the side chain, a hexanoyl substituent attached to the 25-position (C-25) in the side chain, and the carbon atoms of the methyl groups normally located at the 26 and 27 positions (C-26 and C-27) in the side chain bonded together to form a three member ring with the carbon atom at position 25 in the side chain. These compounds may also be named, and may be referred to herein, especially in the description of their synthesis herein and the Schemes, as 2-methylene-(22E)-25-hexanoyl-24-oxo-26,27-cyclo-22-dehydro-19-nor-vitamin D analogs. The preferred vitamin D analog is 2-methylene-(22E)-25-hexanoyl-24-oxo-26,27-cyclo-22-dehydro-19-nor-lot-hydroxyvitamin $D_3$ (hereinafter referred to as "UW-05").

Structurally these 2-methylene-(22E)-25-hexanoyl-24-oxo-26,27-cyclo-22-dehydro-19-nor-vitamin D analogs are characterized by the general formula I shown below:

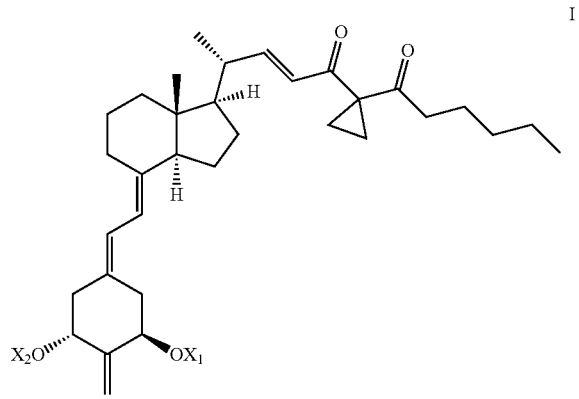

where $X_1$ and $X_2$, which may be the same or different, are each selected from hydrogen or a hydroxy-protecting group. The preferred analog is 2-methylene-(22E)-25-hexanoyl-24- oxo-26,27-cyclo-22-dehydro-19-nor-1α-hydroxyvitamin $D_3$ which has the following formula Ia:

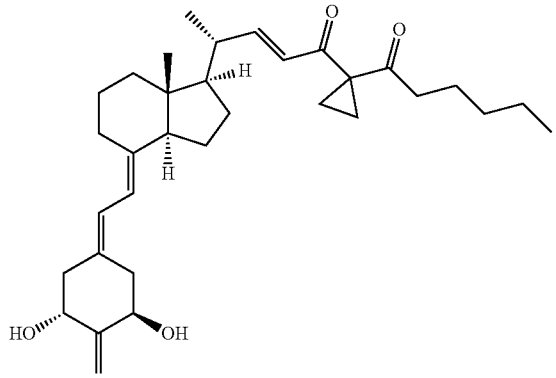

The above compounds I, particularly Ia, exhibit a desired, and highly advantageous, pattern of biological activity. These compounds are characterized by relatively high binding to vitamin D receptors, which is only slightly less than that of the native hormone 1α,25-dihydroxyvitamin $D_3$. These compounds also have excellent ability to promote intestinal calcium transport in vivo. These compounds I, and particularly Ia, also have some ability to mobilize calcium from bone in a dose dependent manner, but they would be classified as having much lower bone calcium mobilizing activity as compared to 1α,25-dihydroxyvitamin $D_3$. It is undesirable to raise serum calcium to supraphysiologic levels when suppressing the preproparathyroid hormone gene (Darwish & DeLuca, Arch. Biochem. Biophys. 365, 123-130, 1999) and parathyroid gland proliferation. These analogs having relatively low bone calcium mobilization activity while very active on cell differentiation are expected to be useful as a therapy for suppression of secondary hyperparathyroidism of renal osteodystrophy.

The compounds I, particularly Ia, of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I, and particularly Ia, are also characterized by relatively high cell differentiation activity and in promoting transcription. Thus, these compounds also provide a therapeutic agent for the treatment of psoriasis, or as an anti-cancer agent, especially against leukemia, colon cancer, breast cancer, skin cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject.

One or more of the compounds may be present in a composition to treat the above-noted diseases and disorders in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually or parenterally in dosages of from about 0.01 μg/day to about 1000 μg/day, preferably from about 0.1 μg/day to about 500 μg/day.

BRIEF DESCRIPTION OF THE DRAWINGS

In the drawings:

FIGS. 1-5 illustrate various biological activities of 2-methylene-(22E)-25-hexanoyl-24-oxo-26,27-cyclo-22-dehydro-19-nor-1α-hydroxyvitamin herein referred to as "UW-05", as compared to the native hormone 1α,25-dihydroxyvitamin hereinafter "1,25$(OH)_2D_3$."

FIG. 1 is a graph illustrating the relative activity of UW-05 and 1,25$(OH)_2D_3$ to compete for binding with [$^3$H]-1,25-$(OH)_2$-$D_3$ to the full-length recombinant rat vitamin D receptor;

FIG. 2 is a graph illustrating the percent RL-60 cell differentiation as a function of the concentration of UW-05 and 1,25$(OH)_2D_3$;

FIG. 3 is a graph illustrating the in vitro transcription activity of 1,25$(OH)_2D_3$ as compared to UW-05;

Figure 1:
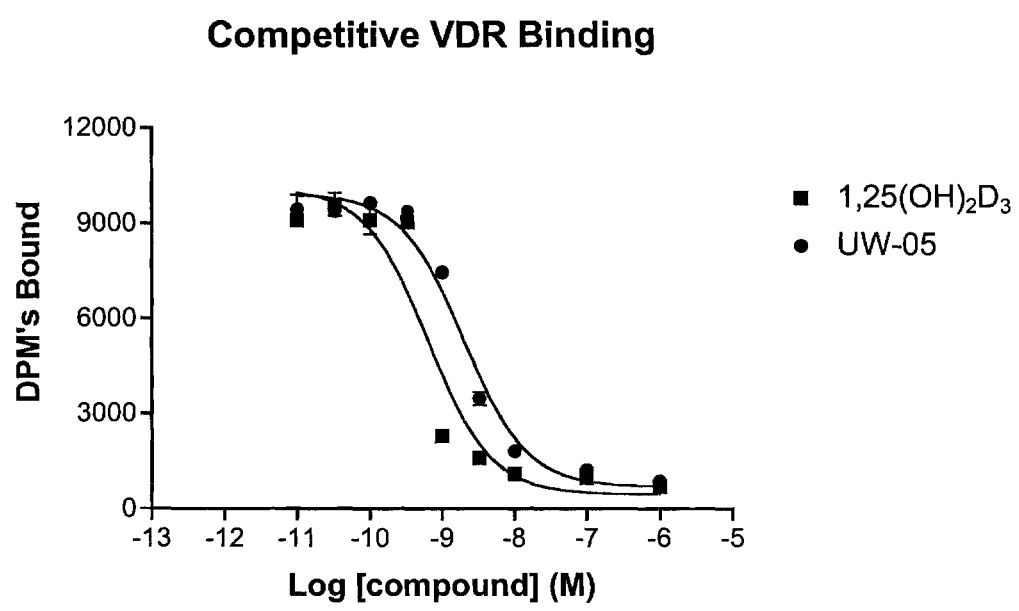

DETAILED DESCRIPTION OF THE INVENTION 2-methylene-(22E)-25-hexanoyl-24-oxo-26,27-cyclo-22-dehydro-19-nor-1α-hydroxyvitamin $D_3$ (referred to herein as "UW-05") a 19-nor vitamin D analog which is characterized by the presence of a methylene substituent at the carbon 2 (C-2), an oxo group attached to carbon 24 (C-24) of the side chain, a double bond located between carbon atom positions 22 and 23 in the side chain, a hexanoyl substituent attached to the 25-position (C-25) in the side chain, and the carbon atoms of the methyl groups normally located at the 26 and 27 positions (C-26 and C-27) in the side chain bonded together to form a three member ring with the carbon atom at position 25 in the side chain, was synthesized and tested. Such vitamin D analog seemed an interesting target because the relatively small methylene group at the C-2 position should not interfere with binding to the vitamin D receptor. Structurally, this 19-nor analog is characterized by the general formula Ia previously illustrated herein, and its pro-drug (in protected hydroxy form) is characterized by general formula I previously illustrated herein.

The preparation of 2-methylene-(22E)-25-hexanoyl-24-oxo-26,27-cyclo-22-dehydro-19-nor-vitamin D analogs having the structure I can be accomplished by a common general method, i.e. see Schemes I and II. Scheme I illustrates the method using vitamin $D_2$ as a starting material to generate diol 1 and thereafter ketone 3. Ketone 3 is then condensed with the allylic phosphine oxide 4 to the corresponding 2-methylene-19-nor-vitamin D analog 5 which in turn is converted to alcohol 6 and finally to aldehyde 7, as described hereinafter. The side chain is introduced by reaction of aldehyde 7 with reagent 8 to yield vitamin D analog 9 followed by deprotection at carbon 1 (C-1) and carbon 3 (C-3) to yield the desired compound 10.

In Scheme I, protection of the hydroxy groups is provided by either an acyl group (Ac) or t-butyldimethylsilyl group (TBS). Although Ac and TBS groups are preferred, any hydroxy-protecting group, as hereinafter defined, may be utilized during the reaction steps.

The condensation step in Scheme I forming analog 5 represents an application of the convergent synthesis concept, which has been applied effectively for the preparation of vitamin D compounds [e.g. Lythgoe et al., J. Chem. Soc. Perkin Trans. 1, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

The reagent 8 is not known. It can be prepared by the method shown in Scheme II herein (see the preparation of compound UW-05).

For the preparation of the required phosphine oxides of general structure 4, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where K is an integer.

More specifically, reference should be made to the following illustrative examples and description as well as to Schemes I and II herein for a detailed illustration of the preparation of compound UW-05.

In this example specific products identified by Arabic numerals (1, 2, 3) refer to the specific structures so identified in the Schemes I and II.

EXAMPLES

Chemistry Ultraviolet (UV) absorption spectra were recorded with a Beckman-Coulter DU 530 UV/Vis spectrophotometer in the solvent noted. $^1H$ nuclear magnetic resonance (NMR) spectra were recorded at 400 MHz or 500 MHz with Bruker Instruments DMX-400 and DMX-500 Avance console spectrometers in the solvent noted. $^{13}C$ nuclear magnetic resonance (NMR) spectra were recorded at 101 MHz or 126 MHz with Bruker Instruments DMX-400 and DMX-500 Avance console spectrometers in the solvent noted. Chemical shifts (δ) are reported downfield from internal $Me_4Si$ (δ 0.00). Electon impact (EI) mass spectra were recorded with Micromass AutoSpec (Beverly, Mass.) instrument. High-performance liquid chromatography (HPLC) was performed on a Waters Associates liquid chromatograph equipped with a Model Delta 600 solvent delivery system, a Model 600 Controller, a Rheodyne 7725i injector and a Model 2487 Dual λ Absorbance Detector. Optical rotary values were recorded with Perkin-Elmer Model 343 polarimeter at the concentration and in the solvent noted.

Example 1

Preparation of 2-Methylene-(22E)-25-Hexanoyl-24-Oxo-26,27-Cyclo-22-Dehydro-1α-Hydroxy-19-Nor-Vitamin $D_3$ (Compound UW-05; 10)
(see Scheme I)

Des-A,B-23,24-dinorcholane-8,22-diol (1)

A solution of vitamin $D_2$ (5.00 g; 12.7 mmol) in methanol (400 ml) and pyridine (5 ml) was cooled to −78° C. while purging with argon. The argon stream was stopped and stream of ozone was passed until blue color appeared. The solution was purged with oxygen until blue color disappeared and treated with $NaBH_4$ (1.20 g; 31.7 mmol). After 20 min. the second portion of $NaBH_4$ (1.20 g; 31.7 mmol) was added and reaction was allowed to warm to room temperature. The third portion of $NaBH_4$ (1.20 g; 31.7 mmol) was added and reaction mixture was stirred at room temperature overnight. The reaction was quenched with water (70 ml) and concentrated under vacuum. The residue was extracted with methylene dichloride (3×100 ml). The organic phase was washed with 1M aqueous solution of HCl (2×100 ml), saturated aqueous solution of $NaHCO_3$ (100 ml), dried over anhydrous $MgSO_4$ and concentrated under vacuum. The residue was purified by flash chromatography (25% ethyl acetate/hexane) to yield 2.05 g (9.69 mmol; 76% yield) of diol 1 as white crystals. $[\alpha]_D$=+56.0 (c 0.95, $CHCl_3$); mp 110-111° C.; $^1$H NMR (400 MHz, $CDCl_3$)™ 0.96 (3H, s), 1.03 (3H, d, J=6.6 Hz), 3.38 (1H, dd, J=10.5 Hz, J=6.8 Hz), 3.64 (1H, dd, J=10.5 Hz, J=3.2 Hz), 4.09 (1H, d, J=2.3 Hz); $^{13}$C NMR (101 MHz, $CDCl_3$)™ 13.6, 16.6, 17.4, 22.6, 26.6, 33.5, 38.2, 40.2, 41.3, 52.3, 52.9, 67.8, 69.2; MS (EI) m/z 212 (M$^+$, 2), 194 (17), 179 (18), 163 (10), 135 (19), 125 (34), 111 (100); exact mass calculated for $C_{13}H_{22}O$ ([M–$H_2O$]$^+$) 194.1671, found 194.1665.

Des-A,B-22-(acetoxy)-23,24-dinorcholane-8-ol (2)

To a stirred solution of 1 (54 mg, 0.26 mmol) and triethylamine (50 µL; 36 mg; 0.36 mmol) in methylene dichloride (5 ml) acetic anhydride was added dropwise at –5° C. The reaction mixture was kept at 4° C. overnight. Then methylene dichloride (30 ml) was added and the mixture was washed with water (7 ml). Organic phase was dried over anhydrous $MgSO_4$ and concentrated under reduced pressure to give 65 mg (0.25 mmol; 98% yield) of 2. $[\alpha]_D$=+33.7 (c 0.90, $CHCl_3$); mp 78-80° C.; $^1$H NMR (500 MHz, $CDCl_3$)™ 0.96 (3H, s), 1.00 (3H, d, J=6.6 Hz), 2.05 (3H, s), 3.77 (1H, dd, J=10.6 Hz, J=7.7 Hz), 4.06 (1H, dd, J=10.6 Hz, J=3.3 Hz), 4.11 (1H, br s); $^{13}$C NMR (101 MHz, $CDCl_3$)™ 13.5, 17.0, 17.4, 21.0, 22.5, 26.6, 33.5, 35.3, 40.2, 41.9, 52.3, 53.2, 69.1, 69.4, 171.4; MS (EI) m/z 254 (M$^+$, 2), 236 (5), 205 (2), 194 (12), 176 (22), 161 (14), 135 (16), 125 (34), 111 (100), exact mass (ESI) calculated for $C_{15}H_{23}O_3Na$ ([M+Na]$^+$) 277.1780, found 277.1791.

Des-A,B-22-(acetoxy)-23,24-dinorcholane-8-one (3)

To a stirred solution of 2 (64 mg; 0.25 mmol) and PPTS (10 mg; 0.04 mmol) in methylene dichloride (12 ml) PDC (244 mg; 0.65 mmol) was added at 0° C. Then cooling bath was removed and the reaction mixture was stirred for 2.5 h. After that solvent was removed under reduced pressure and the residue was purified on silica gel Sep-Pack cartridge (15-25% ethyl acetate/hexane) to give 55 mg (0.22 mmol; 87% yield) of 3. $^1$H NMR (400 MHz, $CDCl_3$)™ 0.66 (3H, s), 1.06 (3H, d, J=6.6 Hz), 2.47 (1H, dd, J=11.5 Hz, J=7.6 Hz), 3.82 (1H, dd, J=10.7 Hz, J=7.2 Hz), 4.08 (1H, dd, J=10.7 Hz, J=3.3 Hz); $^{13}$C NMR (101 MHz, $CDCl_3$)™ 12.5, 17.2, 19.2, 21.0, 24.0, 27.0, 35.5, 38.8, 40.9, 49.9, 53.3, 61.6, 69.1, 171.3, 211.6; MS (EI) m/z 252 (M$^+$, 18) 237 (18), 220 (24), 205 (64) 192 (80), 124 (100); exact mass (ESI) calculated for $C_{15}H_{21}O_3Na$ ([M+Na]$^+$) 275.1623, found 275.1631.

(20S)-22-Acetoxy-1α-[(tert-butyldimethylsilyl)oxy]-2-methylene-19-nor-homopregnacalciferol tert-Butyldimethylsilyl Ether (5)

To a stirred solution of 4 (55 mg; 94 µmol) in tetrahydrofuran (700 µl) few drops of 1.7 M solution of phenyl lithium in cyclohexane/ether (7/3) was added at –25° C. until deep orange color persisted. Then stoichiometric amount (50 µl; 85 µmol) of phenyl lithium solution was added. After 20 min. the mixture was cooled down to –78° C. and a solution of 3 (23 mg; 91 µmol) in tetrahydrofuran (300 µl) was siphoned via cannula. After 2 h cooling bath was removed and the reaction mixture was stirred at 4° C. for next 2 h. Then saturated aqueous solution of $NH_4Cl$ (1 ml), brine (1 ml) and water (1 ml) was added and the mixture was extracted with hexane (3×7 ml). Organic phase was dried over anhydrous $MgSO_4$ and concentrated under reduced pressure. The residue was purified on silica gel Sep-Pack cartridge (0-3% ethyl acetate/hexane) to give 25 mg (40 µmol; 44% yield) of 5. $^1$H NMR (400 MHz, $CDCl_3$)™ 0.02 (3H, s), 0.05 (3H, s), 0.06 (3H, s), 0.08 (3H, s), 0.57 (3H, s), 0.86 (9H, s), 0.89 (9H, s), 1.03 (3H, d, J=6.6 Hz), 2.06 (3H, s), 2.18 (1H, dd, J=12.6 Hz, J=8.3 Hz), 2.32 (1H, m), 2.46 (1H, dd, J=12.8 Hz, J=4.5 Hz), 2.52 (1H, dd, J=13.3 Hz, J=5.9 Hz), 2.83 (1H, m), 3.79 (1H, dd, J=10.6 Hz, J=7.5 Hz), 4.10 (1H, dd, J=10.6 Hz, J=3.2 Hz), 4.43 (2H, m), 4.92 (1H, s), 4.97 (1H, s), 5.84 (1H, d, J=11.1 Hz), 6.21 (1H, d, J=11.1 Hz); $^{13}$C NMR (101 MHz, $CDCl_3$)™ –5.12, –4.87, 12.1, 17.3, 18.2, 21.0, 22.3, 23.3, 2×25.8, 27.2, 28.7, 36.2, 38.5, 40.4, 45.7, 47.6, 53.1, 55.9, 69.5, 71.6, 72.5, 106.3, 116.3, 122.3, 133.0, 140.7, 152.9, 171.4; MS (EI) m/z 484 (100), 366 (25), 230 (44); exact mass calculated for $C_{36}H_{64}O_4Si_2$ ([M+Na]$^+$) 639.4241, found 639.4266.

(20S)-1α-[(tert-Butyldimethylsilyl)oxy]-22-hydroxy-2-methylene-19-nor-homopregnacalciferol tert-Butyldimethylsilyl Ether (6)

To a stirred solution of 5 (24 mg, 39 µmol) in methanol (1 ml) 10% sodium methoxide in methanol (150 µl) was added dropwise at 0° C. Cooling bath was removed and the reaction mixture was stirred for min. Diethyl ether (20 ml) was added and the mixture was washed with saturated aqueous solution of $NH_4Cl$ (3 ml) and water (3 ml). Organic phase was dried over anhydrous $MgSO_4$ and concentrated under reduced pressure. The residue was purified on silica gel Sep-Pack cartridge (10% ethyl acetate/hexane) to give 22 mg (38 µmol; 98% yield) of 6. $^1$H NMR (500 MHz, $CDCl_3$)™ 0.02 (3H, s), 0.05 (3H, s), 0.06 (3H, s), 0.08 (3H, s), 0.57 (3H, s), 0.86 (9H, s), 0.89 (9H, s), 1.07 (3H, d, J=6.6 Hz), 2.01 (2H, m), 2.18 (1H, dd, J=12.3 Hz, J=8.9 Hz), 2.30 (1H, m), 2.48 (1H, dd, J=12.6 Hz, J=4.3 Hz), 2.56 (1H, dd, J=13.1 Hz, J=5.6 Hz), 2.84 (1H, m), 3.41 (1H, m), 3.68 (1H, m), 4.42 (2H, m), 4.93 (1H, s), 4.98 (1H, s), 5.85 (1H, d, J=11.2 Hz), 6.25 (1H, d, J=11.2 Hz); $^{13}$C NMR (126 MHz, $CDCl_3$)™ –5.1, –4.9, 12.1, 16.9, 22.3, 23.4, 2×25.8, 27.2, 28.7, 38.6, 39.1, 40.4, 45.7, 47.6, 52.8, 56.0, 68.0, 71.6, 72.5, 106.3, 116.2, 122.3, 140.9, 152.9. MS (EI) m/z 442 (100), 366 (28).

(20S)-α-[(tert-Butyldimethylsilyl)oxy]-2-methylene-22-oxo-19-nor-homopregnacalciferol tert-Butyldimethylsilyl Ether (7)

To a stirred solution of oxalyl chloride (12 µl; 18 mg; 140 µmol) in methylene dichloride (400 µl) precooled solution of dimethyl sulfoxide (40 µl; 44 mg; 560 µmol) in methylene dichloride (300 µl) was added dropwise via cannula at –78° C. After 30 min. a solution of 6 (22 mg; 38 µmol) in methylene dichloride (200 µl) was added via cannula. The reaction mixture was stirred for min. and triethylamine (42 µl; 30 mg; 300 µmol) was added. After next 15 min. cooling bath was removed and the reaction mixture was warmed up to room temperature. Methylene dichloride (15 ml) was then added and the mixture was washed with water (3 ml). Organic phase was dried over anhydrous MgSO$_4$ and concentrated under reduced pressure. The residue was purified on silica gel Sep-Pack cartridge (1-2% ethyl acetate/hexane) to give 17 mg (30 μmol; 78% yield) of 7. $^1$H NMR (400 MHz, CDCl$_3$)™ 0.02 (3H, s), 0.05 (3H, s), 0.06 (3H, s), 0.08 (3H, s), 0.59 (3H, s), 0.86 (9H, s), 0.90 (9H, s), 1.14 (3H, d, J=6.8 Hz), 2.18 (1H, dd, J=12.5 Hz, J=8.4 Hz), 2.85 (1H, m), 4.43 (2H, m), 4.92 (1H, s), 4.97 (1H, s), 5.86 (1H, d, J=11.2 Hz), 6.21 (1H, d, J=11.2 Hz), 9.59 (1H, d, J=3.3 Hz); $^{13}$C NMR (101 MHz, CDCl$_3$)™ −4.8, −4.5, 13.6, 22.5, 23.3, 2×25.8, 26.5, 38.6, 40.3, 47.6, 49.8, 51.4, 55.5, 71.6, 72.5, 106.4, 116.6, 122.2, 133.4, 140.1, 152.9, 205.0.

(22E)-1α-[(tert-Butyldimethylsilyl)oxy]-2-methylene-24-oxo-25-hexanoyl-26,27-cyclo-22-dehydro-19-norvitamin D$_3$ tert-Butyldimethylsilyl Ether (9)

To a stirred solution of 8 (30 mg; 103 μmol) in tetrahydrofuran (250 μl) 1M solution of lithium hexamethyldisilazide in tetrahydrofuran (90 μl; 90 μmol) was added dropwise. After 1 h a solution of 7 (17 mg; 30 μmol) in tetrahydrofuran (200 μl) was added via cannula and the reaction mixture was stirred for 3 days. Then diethyl ether (20 ml) was added and the mixture was washed with saturated aqueous solution of NH$_4$Cl (3 ml) and water (3 ml). Organic phase was dried over anhydrous MgSO$_4$ and concentrated under reduced pressure. The residue was purified on silica gel Sep-Pack cartridge (1-3% ethyl acetate/hexane) and on HPLC (2% ethyl acetate/hexane; Zorbax Rx-Sil 9.4 mm×25 cm; 4 ml/min.; R$_f$=9.2 min.) to give 14 mg (19 μmol; 63% yield) of 9. UV (hexane) $\lambda_{max}$=237, 244, 253, 263 nm; $\Sigma_{max}$=47000; $^1$H NMR (400 MHz, CDCl$_3$)™ 0.02 (3H, s), 0.04 (3H, s), 0.06 (3H, s), 0.08 (3H, s), 0.57 (3H, s), 0.86-0.91 (2H, m), 1.10 (2H, d, J=6.5 Hz), 2.55 (2H, t, J=7.3 Hz), 2.83 (1H, m), 4.42 (2H, m), 4.92 (1H, s), 4.97 (1H, s), 5.83 (1-1H, d, J=11.1 Hz), 6.14 (1H, d, J=15.7 Hz), 6.20 (1H, d, J=11.1 Hz), 6.77 (1H, dd, J=15.7 Hz, J=9.0 Hz); $^{13}$C NMR (101 MHz, CDCl$_3$)™ −5.1, −4.9, 12.3, 13.9, 16.3, 19.3, 22.2, 22.4, 23.3, 23.8, 2×25.8, 27.6, 28.6, 31.3, 38.6, 40.4, 41.6, 47.6, 55.3, 56.0, 71.6, 72.5, 116.5, 122.2, 126.4, 133.2, 140.3, 152.9, 154.8, 196.0, 206.5; MS (EI) m/z 679 (6), 604 (82), 547 (9), 366 (52), 73 (100); exact mass (ESI) calculated for C$_{45}$H$_{76}$O$_4$Si$_2$Na ([M+Na]$^+$) 759.5180, found 759.5164.

(22E)-2-Methylene-24-oxo-25-hexanoyl-26,27-cyclo-22-dehydro-α-hydroxy-19-norvitamin D$_3$ (10)

To a stirred solution of 9 (12 mg; 16 μmol) in ethanol (800 μl) (1S)-(+)-10-camphorsulfonic acid (6 mg; 26 μmol) was added. After 30 h ethyl acetate (15 ml), saturated aqueous solution of NaHCO$_3$ (1.5 ml) and water (1.5 ml) was added. The mixture was extracted with ethyl acetate (3×10 mL). Organic phase was dried over anhydrous MgSO$_4$ and concentrated under reduced pressure. The residue was purified on silica gel Sep-Pack (10-40% ethyl acetate/hexane) to give 6.8 mg (13.5 μmol; 84% yield) of 10. UV (EtOH) $\lambda_{max}$=236, 244, 253, 262 nm; $\Sigma_{max}$=47000; $^1$H NMR (400 MHz, CDCl$_3$)™ 0.58 (3H, s), 0.88 (3H, t, J=7.1 Hz), 1.10 (3H, d, J=6.6 Hz), 1.97-2.05 (1H, m), 2.27-2.36 (3H, m), 2.53-2.60 (3H, m), 2.81-2.86 (2H, m), 4.46-4.50 (2H, m), 5.09 (1H, s), 5.11 (1H, s), 5.88 (1H, d, J=11.2 Hz), 6.14 (1H, d, J=16.6 Hz), 6.35 (1H, d, J=11.2 Hz), 6.77 (1H, dd, J=16.6 Hz, J=9.0 Hz); $^{13}$C NMR (101 MHz, CDCl$_3$)™ 12.4, 13.9, 16.3, 19.3, 22.3, 22.4, 23.2, 23.8, 27.5, 28.9, 31.3, 38.1, 40.2, 40.3, 41.5, 45.8, 46.0, 55.3, 56.0, 70.7, 71.8, 107.8, 115.7, 124.0, 126.5, 130.9, 142.5, 151.9, 154.7, 196.0, 206.5; MS (EI) m/z 508 (M$^+$, 2), 425 (1), 318 (2), 252 (3), 220 (75), 205 (100); exact mass calculated for C$_{33}$H$_{48}$O$_4$ 508.3553, found 508.3556.

Example 2

Preparation of 1-[2-(dimetoxy-phosphoryl)-acetyl]-1-hexanoyl-cyclopropane (Compound 8; see Scheme II)

2,4-Nonanedione (13)

To a stirred solution of methyl acetate 1.1 (27.8 ml; 25.9 g; 350 mmol) in diethyl ether (200 ml) NaH (60% w/w; 4.8 g; 200 mmol) was added and resulted slurry was brought to boiling. Then a solution of 2-heptanone 12 (24.4 ml; 20.0 g; 175 mmol) in diethyl ether (150 ml) was added dropwise over 3 h. Refluxing was maintained for next 5 h. Then 10% aqueous solution of HCl with crushed ice (ca. 100 ml) was added carefully and organic phase was separated. Water phase was extracted with diethyl ether (150 ml) and combined organic phases were washed with saturated aqueous solution of NaHCO$_3$ (50 ml), dried over anhydrous MgSO$_4$ and concentrated under reduced pressure. The residue was purified by distillation under reduced pressure to give 15.6 g (99.7 mmol; 64% yield) of 13. $^1$H NMR (500 MHz, CDCl$_3$)™ 0.90 (3H, m), 1.31 (2H, m), 1.60 (2H, m), 2.05 (2.1H, s), 2.13 (0.3H, s), 2.17 (0.3H, s), 2.24 (0.3H, s), 2.26 (1.4H, t, J=7.5 Hz), 2.42 (0.15H, t, J=7.5 Hz), 2.50 (0.25H, t, J=7.4 Hz), 3.57 (0.25H, s), 5.49 (0.7H, s); $^{13}$C NMR (126 MHz, CDCl$_3$)™ 14.0, 22.5, 22.6, 23.1, 25.0, 25.5, 30.9, 31.2, 31.5, 38.3, 43.8, 58.0, 69.1, 191.5, 194.4, 202.2, 204.3, 204.6; MS (EI) m/z 157 ([M+H]$^+$, 52), 156 (M$^+$, 9), 141 (8), 113 (17), 100 (45), 85 (100); exact mass calculated for C$_9$H$_{16}$O$_2$ 156.1150, found 156.1151.

1-Acetyl-1-hexanoyl-cyclopropane (14)

To a vigorously stirred mixture of 1,2-dibromoethane (9 ml; 21.6 g; 114.9 mmol), K$_2$CO$_3$ (30 g; 225 mmol) and acetone (75 ml) 13 (12.0 g; 76.8 mmol) was added. The reaction mixture was stirred and refluxed for 20 h. Then solids were filtered off and the filtrate was concentrated under reduced pressure. The residue was purified by distillation under reduced pressure to give 6.0 g (11.0 mmol; 43% yield) of 14. $^1$H NMR (500 MHz, CDCl$_3$)™ 0.89 (3H, t, J=7.2 Hz), 1.28 (4H, m), 1.46 (4H, s), 1.58 (2H, m), 2.24 (3H, s), 2.50 (2H, 1, J=7.4 Hz); $^{13}$C NMR (101 MHz, CDCl$_3$)™ 14.0, 17.1, 22.5, 23.7, 28.0, 31.3, 39.8, 43.0, 204.6, 206.6; MS (EI) m/z 183 ([M+H]$^+$, 10), 182 (M$^+$, 4), 164 (6), 139 (29), 126 (69), 111 (100); exact mass calculated for $C_{11}H_{18}O_2$ 182.1307, found 182.1308.

1-Bromoacetyl-1-hexanoyl-cyclopropane (15)

To a stirred solution of 14 (4.20 g; 23.0 mmol) and triethylamine (6.47 ml; 4.66 g; 46.0 mmol) in methylene dichloride (200 ml) triethylsilyl trifluoromethanesulfonate (5.24 ml; 6.07 g; 23.0 mmol) was added dropwise at 0° C. After 30 min. N-bromosuccinimide (4.50 g; 25.3 mmol) was added and cooling bath was removed. Then methylene dichloride (500 ml) was added and the mixture was washed with water (2×100 ml). Organic phase was dried over anhydrous MgSO$_4$ and concentrated under reduced pressure. The residue was purified by column chromatography (2-6% ethyl acetate/hexane) to give 1.40 g (5.37 mmol; 23% yield) of 15. $^1$H NMR (400 MHz, CDCl$_3$)™ 0.90 (3H, t, J=7.2 Hz), 1.23-1.36 (4H, m), 1.54 (2H, m), 1.61 (4H, m), 2.29 (2H, t, J=7.4 Hz), 4.30 (2H, s); $^{13}$C NMR (101 MHz, CDCl$_3$)™ 13.9, 18.6, 22.5, 23.6, 31.3, 34.1, 37.3, 40.1, 64.5, 198.5, 206.0; MS (EI) m/z 206 (6), 204 (6), 191 (8), 189 (8), 181 ([M−Br]$^+$, 24), 169 (100); exact mass calculated for $C_{11}H_{17}O_2$ ([M−Br]$^+$) 181.1229, found 181.1224.

1-[2-(Dimetoxy-phosphoryl)-acetyl]-1-hexanoyl-cyclopropane (8)

A solution of 15 (1.50 g; 5.75 mmol) and trimethyl phosphite (850 [l; 891 mg; 7.18 mmol) in toluene (20 ml) was refluxed for 20 h. Then solvent was distilled off and the residue was purified by column chromatography (2-15% isopropanol/hexane) to give 1.05 g (3.62 g; 63% yield) of 8. $^1$H NMR (400 MHz, CDCl$_3$)™ 0.89 (3H, t, J=7.1 Hz), 1.20-1.34 (4H, m), 1.50 (2H, m), 1.55-1.64 (4H, m), 2.33 (2H, t, J=7.3 Hz), 3.47 (2H, d, J$_{H-P}$=22.2 Hz), 3.77 (6H, d, J$_{H-P}$=11.3 Hz); $^{13}$C NMR (101 MHz, CDCl$_3$)™ 13.9, 18.0, 22.5, 23.5, 31.3, 37.9, 39.1 (d, J$_{C-P}$=130 Hz), 43.1, 53.0 (d, J$_{C-P}$=6.2 Hz), 197.9 (d, J$_{C-P}$=7.0 Hz), 206.3; exact mass calculated for $C_{12}H_{20}O_5P$ ([M−CH$_3$]$^+$) 275.1048, found 275.1055.

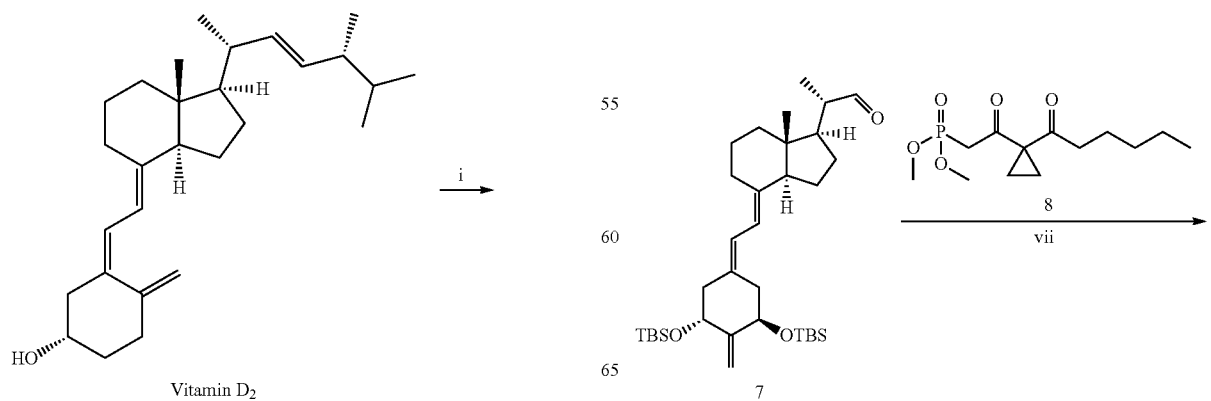

Scheme I

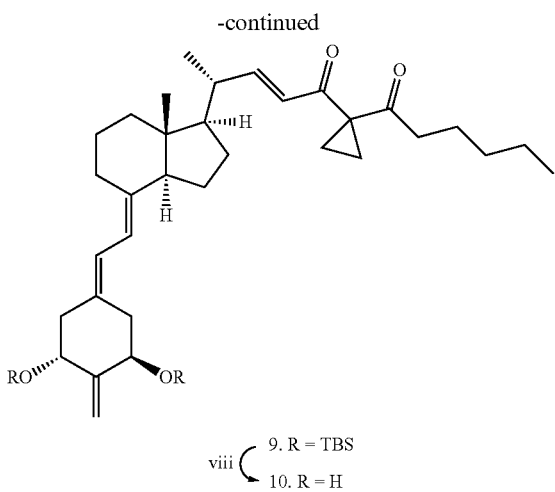

9. R = TBS
10. R = H (i) O₃, MeOH, py; NaBH₄, 76%.
(ii) Ac₂O, Et₃N, DMAP, CH₂Cl₂, 98%.
(iii) PDC, PPTS, CH₂Cl₂, 87%.
(iv) 4, PhLi, THF, 44%.
(v) MeONa/MeOH, 98%.
(vi) DMSO, (COCl)₂, Et₃N, CH₂Cl₂, 78%.
(vii) 8, LiHMDS, THF, 63%.
(viii) CSA, EtOH, 84%.

Scheme II

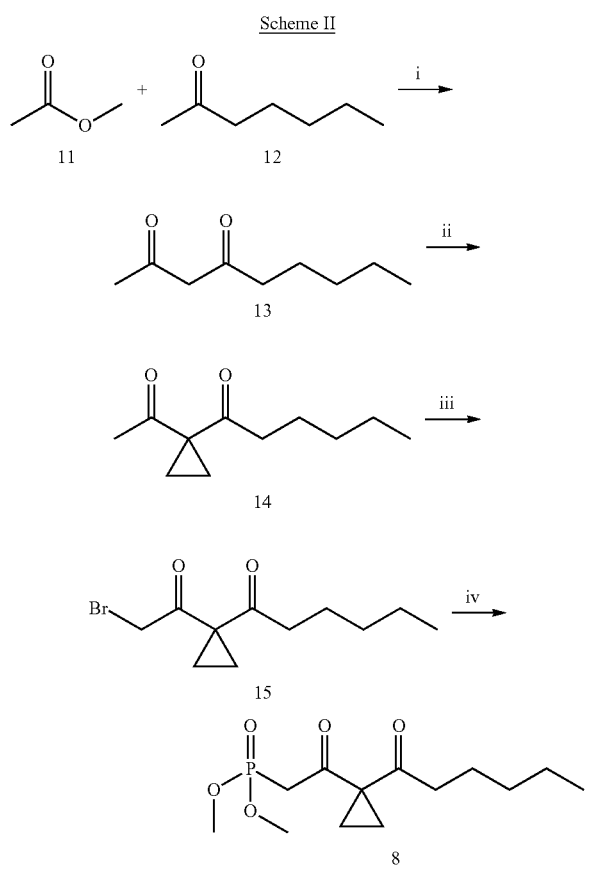

(i) 11, 12, NaH, Et₂O, 64%.
(ii) (CH₂Br)₂, K₂CO₃, AcMe, 43%.
(iii) TESOTf, Et₃N, CH₂Cl₂; NBS, 25%.
(iv) P(OMe)₃, PhMe, 63%.

BIOLOGICAL ACTIVITY OF 2-METHYLENE-(22E)-25-HEXANOYL-24-OXO-26,27-CYCLO-22-DEHYDRO-19-NOR-1α-HYDROXYVITAMIN D₃ (UW-05)

The introduction of a methylene group to the 2-position, an oxo group at carbon 24 of the side chain, a double bond between carbon atoms 22 and 23 in the side chain, a hexanoyl substituent attached to the 25-position (C-25) in the side chain, and the carbon atoms of the methyl groups normally located at the 26 and 27 positions (C-26 and C-27) in the side chain bonded together to form a three member ring with the carbon atom at position 25 in the side chain had little effect on binding to the full length recombinant rat vitamin D receptor, as compared to 1,α25-dihydroxyvitamin D₃. The compound UW-05 bound with almost the same affinity to the nuclear vitamin D receptor as compared to the standard 1,25-(OH)₂D₃ (FIG. 1). It might be expected from these results that compound UW-05 would have equivalent biological activity. Surprisingly, however, compound UW-05 is a highly selective analog with unique biological activity.

Figure 5A:
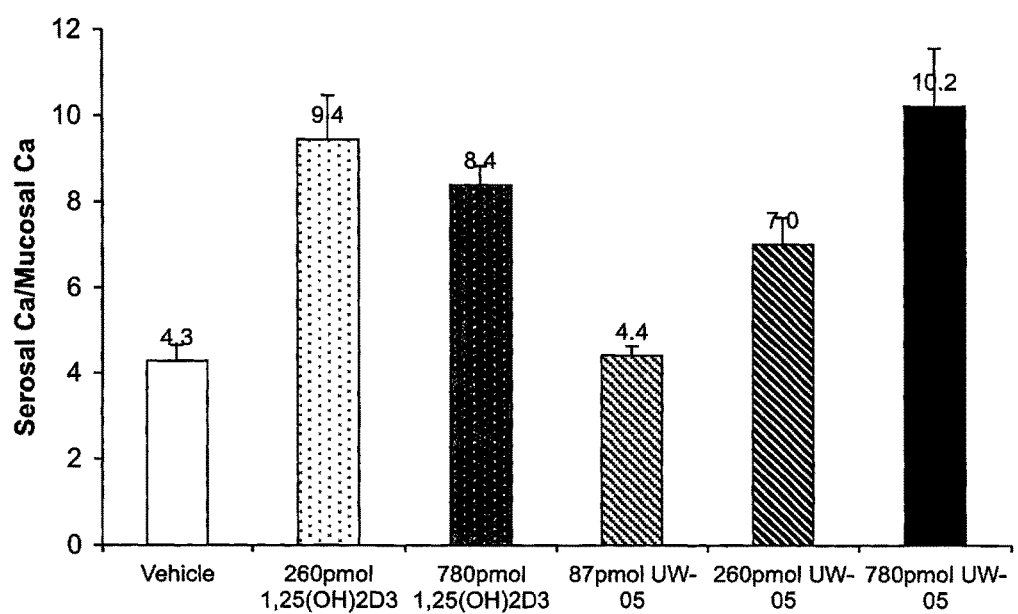
FIG. 5A is a graph illustrating the intestinal calcium transport activity of 1,25$(OH)_2D_3$ as compared to UW-05 in a first group of animals.
Figure 5B:
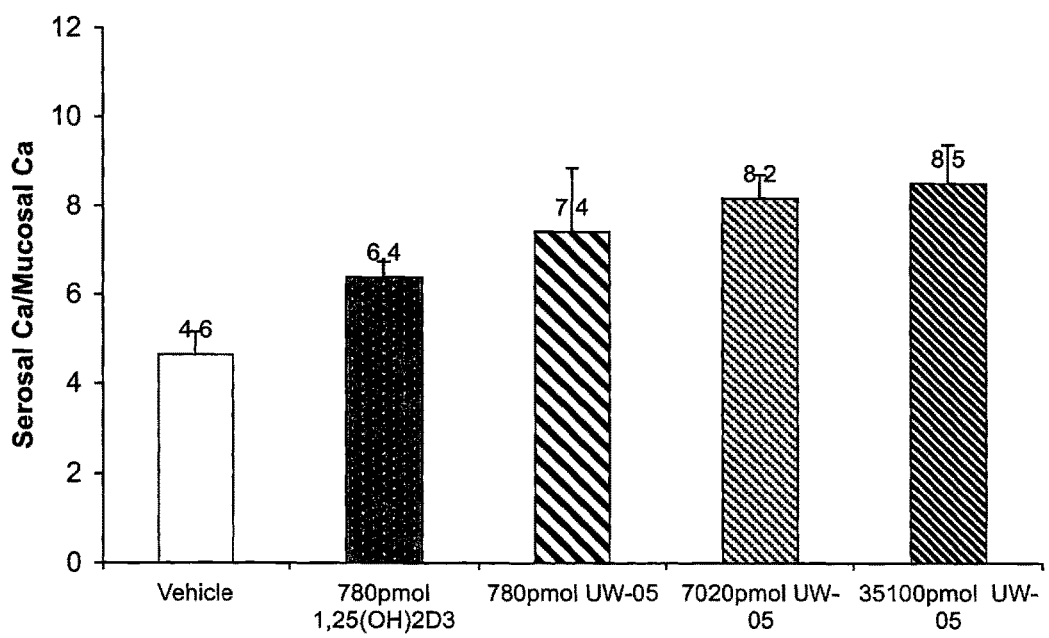
FIG. 5B is a graph illustrating the intestinal calcium transport activity of 1,25$(OH)_2D_3$ as compared to UW-05 in a second group of animals.

FIGS. 5A and 5B show that UW-05 has excellent ability to increase intestinal calcium transport activity in vivo, in a dose dependent manner, approximately equal to 1,25-dihydroxyvitamin D₃ (1,25(OH)₂D₃).

Figure 4A:
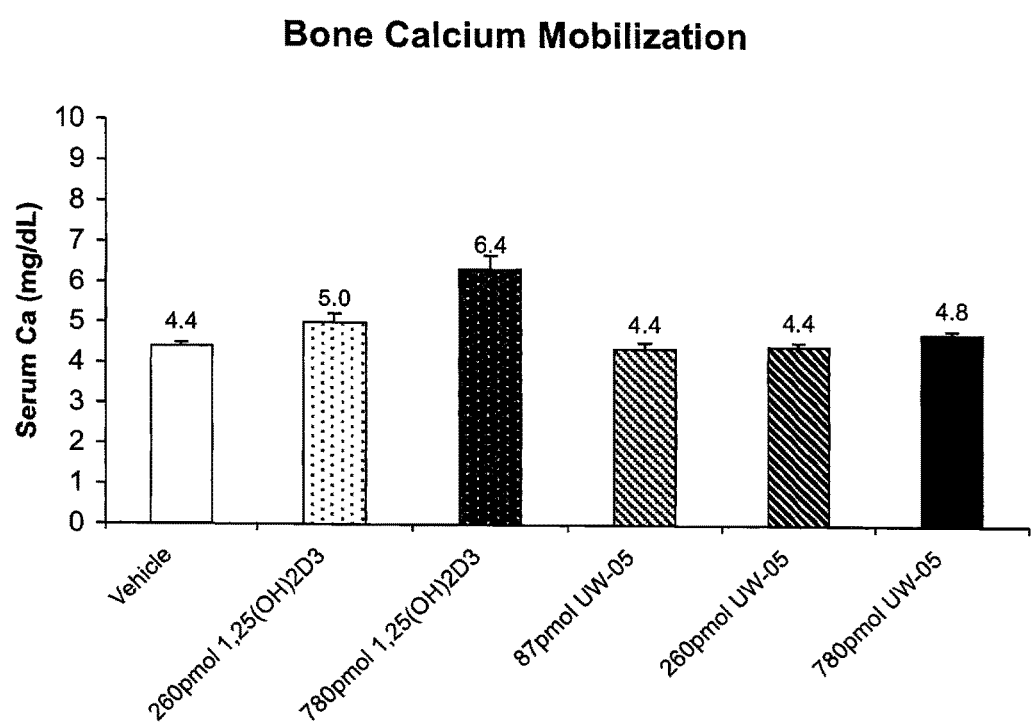
FIG. 4A is a graph illustrating the bone calcium mobilization activity of 1,25$(OH)_2D_3$ as compared to UW-05 in a first group of animals.
Figure 4B:
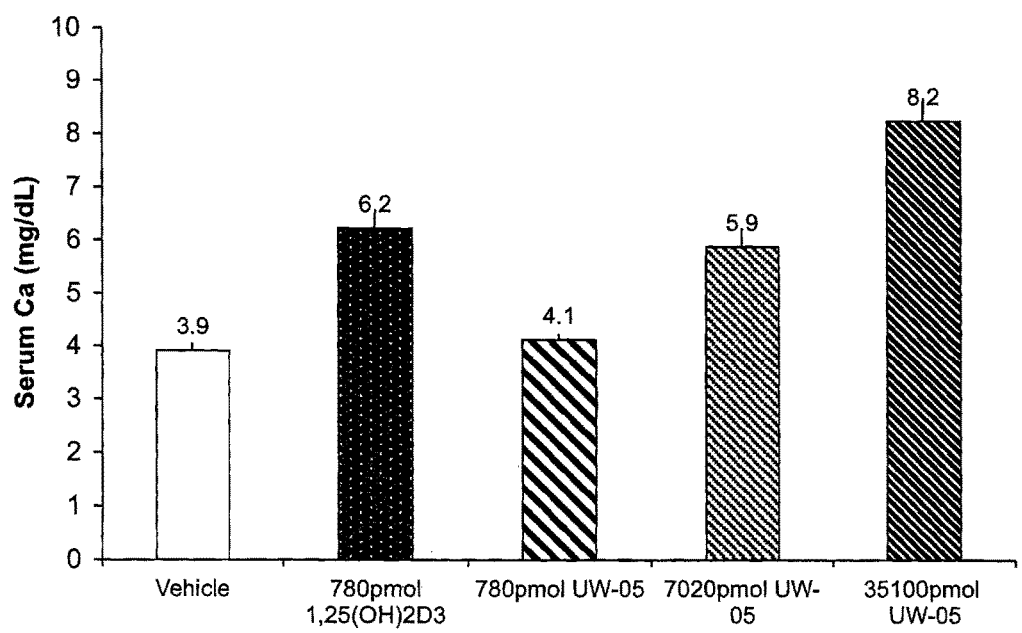
FIG. 4B is a graph illustrating the bone calcium mobilization activity of 1,25$(OH)_2D_3$ as compared to UW-05 in a second group of animals.

FIGS. 4A and 4B demonstrate that UW-05 has about 10 times less bone calcium mobilization activity than 1,25(OH)₂D₃. Although UW-05 has some bone calcium mobilization activity at very high doses, it clearly has significantly lower potency in mobilizing calcium from bone as compared to 1,25(OH)₂D₃, at the recommended lower closes.

FIGS. 4A, 4B, 5A and 5B thus illustrate that UW-05 may be characterized as having significant intestinal calcium transport activity, and relatively low bone calcium mobilization activity.

Figure 2:
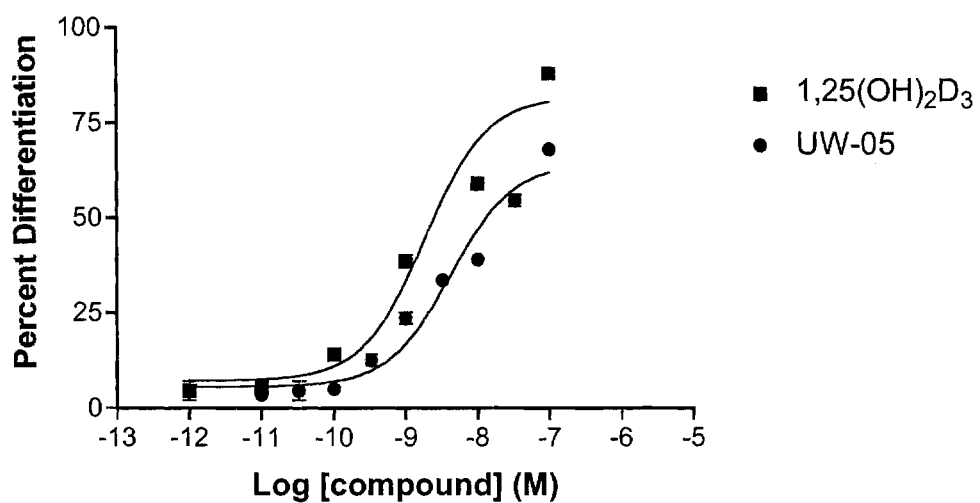

FIG. 2 illustrates that UW-05 has about the same potency as 1,25(OH)₂D₃ on HL-60 cell differentiation, i.e. causing the differentiation of HL-60 cells into monocytes, making it an excellent candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
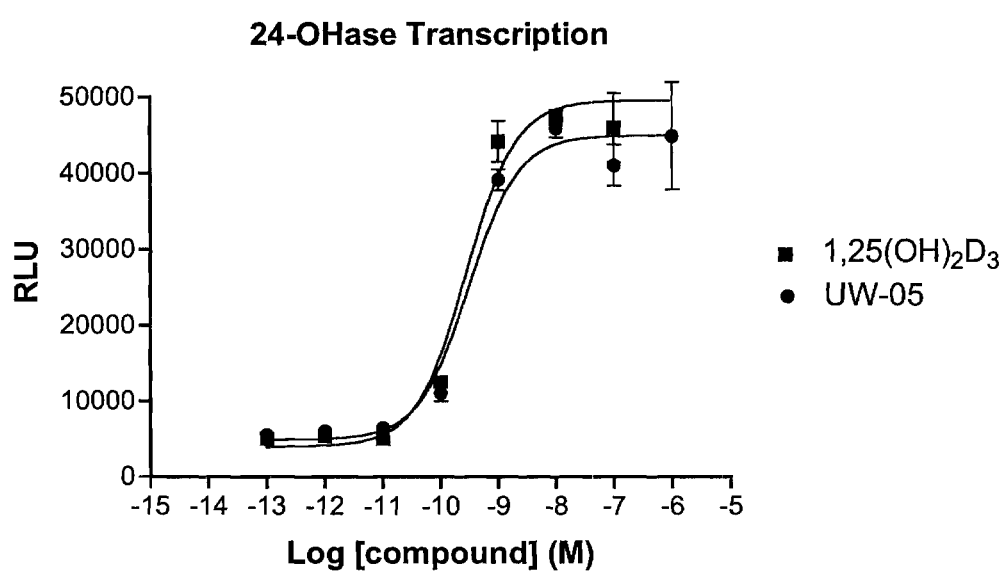

FIG. 3 illustrates that in bone cells the compound UW-05 has about the same potency as 1,25(OH)₂D₃ in increasing transcription of the 24-hydroxylase gene. This result, together with the cell differentiation activity of FIG. 2, suggests that UW-05 will be very effective in psoriasis because it has direct cellular activity in causing cell differentiation, gene transcription, and in suppressing cell growth. These data also indicate that UW-05 may have significant activity as an anti-cancer agent, especially against leukemia, colon cancer, breast cancer, skin cancer and prostate cancer.

The strong activity of UW-05 on HL-60 differentiation suggests it will be active in suppressing growth of parathyroid glands and in the suppression of the preproparathyroid gene.

Experimental Methods

Vitamin D Receptor Binding
Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25(OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapatite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation
Test Material
Study Drugs

The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Intestinal Calcium Transport and Bone Calcium Mobilization

Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Data

Summary of Biological Findings.

The compound UW-05 binds the VDR with only slightly less affinity than the native hormone, and displays equivalent cell differentiation activity and equivalent in vitro gene transcription activity compared to 1,25(OH)$_2$D$_3$. In vivo this compound exhibits significantly less bone calcium mobilization but retains intestinal calcium transport activities. This compound has potential for the treatment of such diseases as cancer, renal osteodystrophy, autoimmune diseases, skin conditions, and psoriasis. While this compound is equally potent compared to 1,25(OH)$_2$D$_3$ in vitro, it shows lower activity in vivo on bone calcium mobilization. UW-05 remains a potentially valuable compound for therapeutic development as it has lower potency in mobilizing calcium from bone storage or stimulating active calcium transport in the intestine, but high potency in cell differentiation and transcription potentially resulting in a compound with a wider safety window than has previously been generated. This increase in safety is exhibited by its increased potency in promoting the differentiation of human promyelocytic cells and gene transcription in bone cells without stimulating bone calcium mobilization and intestinal calcium transport. UW-05 might not only be useful in the treatment of the above listed diseases, but also in the prevention of the above listed diseases.

VDR Binding, HL60 Cell Differentiation, and Transcription Activity.

UW-05 ($K_i$=3×10$^{-10}$M) is almost as active as the natural hormone 1α,25-dihydroxyvitamin D$_3$ ($K_i$=1×10$^{-10}$M) in its ability to compete with [$^3$H]-1,25(OH)$_2$D$_3$ for binding to the full-length recombinant rat vitamin D receptor (FIG. 1). UW-05 also displays about the same activity (EC$_{50}$=4×10$^{-9}$ M) in its ability (efficacy or potency) to promote HL-60 cell differentiation as compared to 1α,25-dihydroxyvitamin D$_3$ (EC$_{50}$=2×10$^{-9}$ M) (See FIG. 2). Also, compound UW-05 (EC$_{50}$=3×10$^{-10}$M) has about the same transcriptional activity in bone cells as 1α,25-dihydroxyvitamin D$_3$ (EC$_{50}$=3×10$^{-10}$M) (See FIG. 3). These results suggest that UW-05 will be very effective in psoriasis because it has direct cellular activity in causing cell differentiation, gene transcription, and in suppressing cell growth. These data also indicate that UW-05 will have significant activity as an anti-cancer agent, especially against leukemia, colon cancer, breast cancer, skin cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism.

Calcium Mobilization from Bone and Intestinal Calcium Absorption in Vitamin D-Deficient Animals.

Using vitamin D-deficient rats on a low calcium diet (0.02%), the activities of UW-05 and $1,25(OH)_2D_3$ in intestine and bone were tested. As expected, the native hormone $(1,25(OH)_2D_3$ increased serum calcium levels at all dosages (FIGS. 4A and 4B). The study reported in FIG. 4A shows that UW-05 has relatively low, or little, activity in mobilizing calcium from bone. It took administration of 780 pmol/day for 4 consecutive days to obtain about the same mobilization of bone calcium as the native hormone $1,25(OH)_2D_3$ did at only 260 pmol/day.

The study reported in FIG. 4B also shows that UW-05 has relatively low, or little, activity in mobilizing calcium from bone. Administration of 7020 pmol/day for 4 consecutive days resulted in about the same mobilization of bone calcium as the native hormone $1,25(OH)_3$ did at only 780 pmol/day, and when the amount of UW-05 was 780 pmol/day no substantial effect was seen.

Intestinal calcium transport was evaluated in the same groups of animals using the everted gut sac method (FIGS. 5A and 5B). The study reported in FIG. 5A shows that UW-05 has relatively significant intestinal calcium transport activity. Although administration of 87 pmol/day for 4 consecutive days did not result in substantial activity, when the amount of UW-05 was increased to 260 pmol/day and then to 780 pmol/day a significant increase in effect was seen.

The study reported in FIG. 5B confirms that UW-05 has the ability to increase intestinal calcium transport activity, and its activity is significant as compared to $1,25(OH)_3D_3$.

These results show that the compound UW-05 promotes intestinal calcium transport when administered at 260 pmol/day. Thus, it may be concluded that UW-05 has significant intestinal calcium transport activity at the recommended lower doses.

These results illustrate that UW-05 is an excellent candidate for numerous human therapies as described herein, and that it may be particularly useful in a number of circumstances such as suppression of secondary hyperparathyroidism of renal osteodystrophy, autoimmune diseases, cancer, numerous types of skin conditions, and psoriasis. UW-05 is an excellent candidate for treating psoriasis because: (1) it has significant VDR binding, transcription activity and cellular differentiation activity; (2) it has little hypercalcemic liability at relatively low doses, unlike $1,25(OH)_2D_3$; and (3) it is easily synthesized. Since UW-05 has significant binding activity to the vitamin D receptor, but has little ability to raise blood serum calcium, it may also be particularly useful for the treatment of secondary hyperparathyroidism of renal osteodystrophy.

These data also indicate that the compound UW-05 of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound UW-05 of the invention.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I, particularly UW-05, may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly UW-05, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly UW-05, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly UW-05, as defined by the above formula I and Ia as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually, or parenterally in dosages of from about 0.01 µg/day to about 1000 µg/day, and preferably from about 0.1 µg/day to about 500 µg/day.

The compounds I, particularly UW-05, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly UW-05, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single close which is capable of being administered to a patient as a physically and chemically stable unit dose comprising either the active ingredient as such or a mixture of it with solid or liquid pharmaceutical diluents or carriers.

We claim:

1. A method of treating psoriasis comprising administering to a subject with psoriasis an effective amount of 2-methylene-(22E)-25-hexanoyl-24-oxo-26,27-cyclo-22-dehydro-19-nor-1α-hydroxyvitamin $D_3$.

2. The method of claim 1 wherein the compound is administered orally.

3. The method of claim 1 wherein the compound is administered parenterally.

4. The method of claim 1 wherein the compound is administered transdermally.

5. The method of claim 1 wherein the compound is administered topically.

6. The method of claim 1 wherein the compound is administered rectally.

7. The method of claim 1 wherein the compound is administered nasally.

8. The method of claim 1 wherein the compound is administered sublingually.

9. The method of claim 1 wherein the compound is administered in a dosage of from about 0.01 μg/day to about 1000 μg/day.

10. A method of treating a disease selected from the group consisting of leukemia, colon cancer, breast cancer, skin cancer or prostate cancer comprising administering to a subject with said disease an effective amount of 2-methylene-(22E)-25-hexanoyl-24-oxo-26,27-cyclo-22-dehydro-19-nor-1α-hydroxyvitamin $D_3$.

11. The method of claim 10 wherein the compound is administered orally.

12. The method of claim 10 wherein the compound is administered parenterally.

13. The method of claim 10 wherein the compound is administered transdermally.

14. The method of claim 10 wherein the compound is administered rectally.

15. The method of claim 10 wherein the compound is administered nasally.

16. The method of claim 10 wherein the compound is administered sublingually.

17. The method of claim 10 wherein the compound is administered in a dosage of from about 0.01 μg/day to about 1000 μg/day.

18. A method of treating an autoimmune disease selected from the group consisting of multiple sclerosis, lupus, diabetes mellitus, host versus graft rejection, and rejection of organ transplants, comprising administering to a subject with said disease an effective amount of 2-methylene-(22E)-25-hexanoyl-24-oxo-26,27-cyclo-22-dehydro-19-nor-1α-hydroxyvitamin $D_3$.

19. The method of claim 18 wherein the compound is administered orally.

20. The method of claim 18 wherein the compound is administered parenterally.

21. The method of claim 18 wherein the compound is administered transdermally.

22. The method of claim 18 wherein the compound is administered rectally.

23. The method of claim 18 wherein the compound is administered nasally.

24. The method of claim 18 wherein the compound is administered sublingually.

25. The method of claim 18 wherein the compound is administered in a dosage of from about 0.01 μg/day to about 1000 μg/day.

26. A method of treating a skin condition selected from the group consisting of wrinkles, lack of adequate skin firmness, lack of adequate dermal hydration and insufficient sebum secretion which comprises administering to a subject with said skin condition an effective amount of a 2-methylene-(22E)-25-hexanoyl-24-oxo-26,27-cyclo-22-dehydro-19-nor-1α-hydroxyvitamin $D_3$.

27. The method of claim 26 wherein the compound is administered orally.

28. The method of claim 26 wherein the compound is administered parenterally.

29. The method of claim 26 wherein the compound is administered transdermally.

30. The method of claim 26 wherein the compound is administered topically.

31. The method of claim 26 wherein the compound is administered rectally.

32. The method of claim 26 wherein the compound is administered nasally.

33. The method of claim 26 wherein the compound is administered sublingually.

34. The method of claim 26 wherein the compound is administered in a dosage of from about 0.01 µg/day to about 1000 µg/day.

35. A method of treating renal osteodystrophy comprising administering to a subject with renal osteodystrophy an effective amount of 2-methylene-(22E)-25-hexanoyl-24-oxo-26,27-cyclo-22-dehydro-19-nor-1α-hydroxyvitamin $D_3$.

36. The method of claim 35 wherein the compound is administered orally.

37. The method of claim 35 wherein the compound is administered parenterally.

38. The method of claim 35 wherein the compound is administered transdermally.

39. The method of claim 35 wherein the compound is administered rectally.

40. The method of claim 35 wherein the compound is administered nasally.

41. The method of claim 35 wherein the compound is administered sublingually.

42. The method of claim 35 wherein the compound is administered in a dosage of from about 0.01 µg/day to about 1000 µg/day.

43. A method of treating obesity of an animal, inhibiting adipocyte differentiation, inhibiting SCD-1 gene transcription, and/or reducing body fat in an animal comprising administering to an animal in need thereof an effective amount of 2-methylene-(22E)-25-hexanoyl-24-oxo-26,27-cyclo-22-dehydro-19-nor-1α-hydroxyvitamin $D_3$.

44. The method of claim 43 wherein the compound is administered orally.

45. The method of claim 43 wherein the compound is administered parenterally.

46. The method of claim 43 wherein the compound is administered transdermally.

47. The method of claim 43 wherein the compound is administered rectally.

48. The method of claim 43 wherein the compound is administered nasally.

49. The method of claim 43 wherein the compound is administered sublingually.

50. The method of claim 43 wherein the compound is administered in a dosage of from about 0.01 µg/day to about 1000 µg/day.

51. The method of claim 43 wherein the animal is a human.

52. The method of claim 43 wherein the animal is a domestic animal.

53. The method of claim 43 wherein the animal is an agricultural animal.

* * * * *

UNITED STATES PATENT AND TRADEMARK OFFICE
CERTIFICATE OF CORRECTION

PATENT NO. : 10,479,764 B2
APPLICATION NO. : 13/533018
DATED : November 19, 2019
INVENTOR(S) : DeLuca et al.

It is certified that error appears in the above-identified patent and that said Letters Patent is hereby corrected as shown below:

In the Specification

Column 1, Line 47, "(1.993)" should be --(1993)--.

Column 2, Line 44, "nor-lot-hydroxyvitamin" should be --nor-1α-hydroxyvitamin--.

Column 4, Line 31, "hydroxyvitamin herein" should be --hydroxyvitamin $D_3$ herein--.

Column 4, Line 33, "hydroxyvitamin herein" should be --hydroxyvitamin $D_3$ herein--.

Column 4, Line 38, "RL-60" should be --HL-60--.

Column 6, Line 36, "(6)" should be --(δ)--.

Column 8, Line 35, "for min." should be --for 30 min.--.

Column 8, Line 66, "for min." should be --for 15 min.--.

Column 10, Line 28, "acetate 1.1" should be --acetate 11--.

Column 10, Line 66, "2H, 1, J=7.4" should be --2H, t, J=7.4--.

Column 14, Line 34, "closes" should be --doses--.

Column 17, Line 15, "(1,25(OH)$_2$D$_3$ increased" should be --(1,25(OH)$_2$D$_3$) increased--.

Column 19, Line 51, "close" should be --dose--.

Signed and Sealed this
Fourteenth Day of January, 2020

Andrei Iancu
*Director of the United States Patent and Trademark Office*